United States Patent
Wells

(10) Patent No.: US 7,113,266 B1
(45) Date of Patent: Sep. 26, 2006

(54) FLOW CYTOMETER FOR DIFFERENTIATING SMALL PARTICLES IN SUSPENSION

(75) Inventor: Mark A. Wells, Davie, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 15 days.

(21) Appl. No.: 11/094,723

(22) Filed: Mar. 30, 2005

(51) Int. Cl.
*G01N 21/00* (2006.01)
*G01N 15/02* (2006.01)

(52) U.S. Cl. .................. 356/73; 356/336; 356/342; 356/369

(58) Field of Classification Search .................. 356/73, 356/336, 342, 369
See application file for complete search history.

(56) References Cited

U.S. PATENT DOCUMENTS 5,798,827 A * 8/1998 Frank et al. .................. 356/39
6,228,652 B1 * 5/2001 Rodriguez et al. ............ 436/63
6,713,019 B1   3/2004 Ozasa et al.
6,794,671 B1 * 9/2004 Nicoli et al. ................. 250/574
2005/0112541 A1 * 5/2005 Durack et al. .................. 435/2

* cited by examiner

Primary Examiner—Layla G. Lauchman
Assistant Examiner—Roy M. Punnoose
(74) Attorney, Agent, or Firm—Warren W. Kutz; Mitchell R. Alter

(57) ABSTRACT

A flow cytometer includes an optical flow cell through which particles to be characterized on the basis of at least their respective side-scatter characteristics are caused to flow seriatim. A plane-polarized laser beam produced by a laser diode is used to irradiate the particles as they pass through a focused elliptical spot having its minor axis oriented parallel to the particle flow path. Initially, the plane of polarization of the laser beam extends perpendicular to the path of particles through the flow cell. A half-wave plate or the like is positioned in the laser beam path to rotate the plane of polarization of the laser beam so that it is aligned with the path of particles before it irradiated particles moving along such path.

12 Claims, 3 Drawing Sheets

FLOW CYTOMETER FOR DIFFERENTIATING SMALL PARTICLES IN SUSPENSION

BACKGROUND OF THE INVENTION

1. Field of the Invention

The present invention relates to improvements in flow cytometers of the type commonly used to differentiate small particles, e.g., various types of blood cells, in a liquid suspension. More particularly, this invention relates to improvements in flow cytometers of the type that use plane-polarized radiation, e.g., that emitted from laser diodes, to irradiate individual particles passing through an optical flow cell in order to detect the light-scattering characteristics of such particles and thereby characterize each particle as being a member of a particular class or type.

2. The Prior Art

Flow cytometers are commonly used to differentiate individual small particles of different types in a particle suspension on the basis of the light-scattering and/or fluorescence characteristics of each particle. Such instruments generally include an optically-transparent flow cell having a particle-interrogation zone through which particles from the sample are made to pass in single file; a laser light source for irradiating such particles, one-at-a-time, as they pass through the particle-interrogation zone; and a plurality of optical detectors that are strategically located about the flow cell to receive both scattered radiation from the irradiated particles, and fluorescence radiation emitted by fluorochromes that have been previously attached to certain particles in a class or of a type of interest. Typically, the photodetectors are positioned to detect both forwardly-scattered radiation within angular ranges determined by the geometry of the light-sensitive elements of the photodetector, and side-scattered radiation that is scattered in direction substantially perpendicular to the directions of the irradiating laser beam and of the particle path. The respective outputs of the photodetectors are then processed in a known manner to identify each of the irradiated particles as a member of a particular class or type. Usually, the flow cytometer provides a histogram or scattergram indicating the number of particles in each class or of each type.

In flow cytometers of the above type, it is becoming increasingly common to employ laser diodes as the particle-irradiating laser light source. Such solid-state devices are often preferred over the more conventional gas lasers, e.g., helium-neon and argon lasers, on the basis of size and economic considerations. Being of relatively small size, these devices can be easily positioned and oriented within the instrument housing to achieve any of various design objectives. While laser diodes may be considered advantageous in many respects, they are not without disadvantages. For example, in addition to being relatively low-power devices, laser diodes typically emit non-collimated radiation that must be collimated for practical use. In most devices, the output radiation emitted from the active semi-conductive element or "die" tends to diverge relatively quickly and, since the die is usually rectangular in shape, the emitted radiation diverges differentially in mutually perpendicular planes. Thus, the radiant output from a laser diode is commonly in the form of an expanding ellipse that typically expands in one plane at a relatively large angle of divergence of, say, 30 degrees, while expanding in a perpendicular plane at a much smaller angle of divergence of, say, 10 degrees. To capture and collimate the laser energy in this expanding beam, it is common to position a collimating lens of relatively high numerical aperture in close proximity to the laser source. While this collimating lens readily collects all of the energy diverging from the source at the smaller angle, it often truncates a portion of the beam diverging at the larger angle. In many laser diodes, the result of this truncation is that a pair of extraneous or spurious light sources (or far-field diffraction patterns) composed of diffracted and/or reflected light appear at the opposing sides of the collimating lens where the beam-truncation occurs. While these spurious light sources are usually of relatively low intensity compared to the collimated main beam, they can be problematic to the performance of a flow cytometer. For example, when focusing the output beam from a laser diode to an elliptical spot adapted to irradiate particles moving through a flow cell, the focused elliptical spot will be accompanied by a pair of relatively faint and ill-defined lobes of radiation or "light-lobes" representing the focused spurious beams of radiation emanating from opposite sides of the collimating lens. These light-lobes appear on opposite sides and outside the boundary of the focused elliptical spot. In the event these light-lobes are positioned in the particle path, they will give rise to low-level light-scatter and fluorescence signals that act to complicate the signal processing of the flow cytometer. Specifically, such low-level signals appear to emanate from small particles that, in fact, are not present in the particle sample.

In U.S. Pat. No. 6,713,019 to Ozasa et al., the above-noted light-lobe problem is addressed by simply adjusting the orientation of a laser diode in a flow cytometer so that the above-noted light-lobes are located outside the particle path through the flow cell, i.e., to position the lobes in a plane that is perpendicular to the particle path. Ozasa et al. note that it is conventional to orient a laser diode in a flow cytometer so that the major axis of the expanding ellipse is parallel to the direction of particle flow through the flow cell (which is normally vertical). This orientation of the laser diode enables the beam to be focused, upon passing through the combination of a cylindrical lens and a condensing lens, to a particle-irradiating ellipse that is (a) diffraction-limited in a plane parallel to its minor axis, and (b) centered on the nominal particle path within the flow cell with it minor axis extending parallel to such path. Because the focused ellipse is diffraction-limited in a plane parallel to the particle path, the flux density of the focused beam is maximized which, in turn, enhances the light-scatter and fluorescence detection sensitivity of the instrument. Also, being diffraction-limited in a plane parallel to the particle path, the focused ellipse prevents the simultaneous irradiation (and detection) of multiple particles traveling relatively close together in the time domain, i.e., in the direction of particle flow. But, as noted by Ozasa et al., a significant drawback of this conventional orientation of a laser diode in a flow cytometer is that it acts to position the above-noted light-lobes directly in the particle path, causing the detectors to mistakenly detect and count small particles that do not, in fact, exist. Ozasa et al.'s solution to this problem, as indicated above, is simply to rotate the laser diode by 90 degrees relative to its support housing so that the major axis of the expanding ellipse is now horizontal, i.e., perpendicular to the (normally vertical) particle path through the flow cell. This has the effect of shifting the lobe radiation outside the particle path, on opposite sides thereof. As a result of this orientation, the particles passing through flow cell are not irradiated by the light lobes and, hence, cannot scatter radiation or emit fluorescent radiation as a result of such irradiation. Thus, there is no need to compensate for the presence of such lobe radiation in the respective outputs of the photodetectors.

Note, while such an orientation of the laser diode would result in a 90 degree rotation of the focused elliptical spot, causing its major axis to be undesirably aligned with the particle path, Ozasa et al. avoids this situation by adding an additional lens to the beam-shaping optical system. The additional lens operates to restore the shape of the focused ellipse to that occurring before the rotation of the laser diode, i.e., to an ellipse in which the minor axis is parallel to the particle path.

While the orientation of the laser diode taught in the Ozasa et al. patent may solve the light-lobe problem identified, it has been observed to create another optical problem affecting the detection of radiation scattered by the irradiated particles. More specifically, when it is desirable to detect side-scatter radiation from the irradiated particles (i.e., radiation scattered at 90 degrees relative to both the optical axis of the irradiating beam and to the particle path through the flow cell), it has been observed that the suggested (horizontal) orientation of the laser diode has the effect of dramatically reducing the signal-to noise ratio (SNR) of the side-scatter signal. The extent of this SNR reduction is such that the side-scatter parameter cannot be used as part of the particle characterization process.

SUMMARY OF THE INVENTION

In view of the foregoing discussion, an object of this invention is to provide a solution to the problem identified, i.e., the problem of detecting side-scattered radiation when a laser diode is so oriented that the major axis of its expanding elliptical output beam is perpendicular to the particle path through the flow cell.

In accordance with one aspect of the invention, it is recognized that the output beam from a laser diode is plane-polarized in the plane in which the beam is diverging the fastest. Further, it is recognized that measurement of side-scattered radiation in a flow cytometer requires that the plane of polarization of the irradiating laser beam must be parallel to the direction of the particle path through the flow cell. Still further, it is recognized that in a flow cytometer of the type described above, i.e., one in which the orientation of a laser diode has been rotated by 90 degrees so as to eliminate the "light lobe" problem identified, the plane of polarization of the particle-irradiating laser beam is no longer parallel to the particle path and, hence, the ability to detect side-scattered radiation is compromised. Thus, in order to make side-scatter measurements with such an instrument, it is necessary to re-establish the requisite relationship between the plane of polarization of the irradiating beam and the particle path.

In view of the above, a flow cytometer structured in accordance with the present invent comprises the following elements: (a) an optical flow cell having a particle-interrogation zone through which particles to be characterized can be made to pass, one-at-a-time, along a substantially linear particle path; (b) a laser source for producing a plane-polarized laser beam, such laser being oriented so that the plane of polarization of its laser beam is perpendicular to the particle path; (c) a beam-shaping lens system for focusing the laser beam as an elliptical spot centered on the particle path within the particle-interrogation zone, the minor axis of such elliptical spot being arranged parallel to the particle path; (d) a side-scatter photodetector positioned to detect a portion of the laser beam upon being scattered by particles irradiated by the focused elliptical spot in a direction substantially perpendicular to the particle path and to the direction from which the laser beam irradiates a particle at the particle-interrogation zone; and (e) a polarization-rotating optical element positioned in the laser beam path between the laser source and the optical flow cell, such optical element serving to rotate the plane of polarization of the laser beam to such an extent that the plane of polarization is arranged substantially parallel to the particle path, rather than perpendicular to such path, as in the prior art system. Preferably, the polarization-rotating optical element comprises either a half-wave plate, or the combination of two quarter-wave plates, which serves to rotate the plane of polarization of the laser beam by 90 degrees.

The invention and its advantages will be better understood from the ensuing detailed description of preferred embodiments, reference being made to the accompanying drawings in which like reference characters denote like parts.

DETAILED DECRIPTION OF PREFERRED EMBODIMENTS

Figure 1:
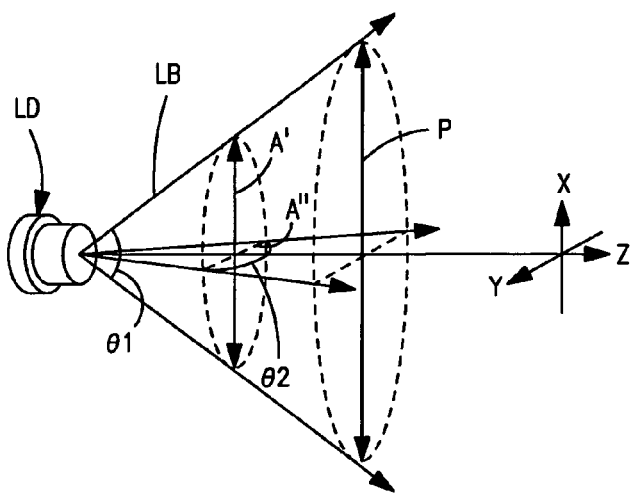
FIG. 1 illustrates the diverging output beam from a conventional laser diode.

Referring now to the drawings, FIG. 1 schematically illustrates a conventional laser diode LD of the type that emits a diverging laser beam LB having an elliptical cross-section that expands in size in accordance with two different angles of divergence, $\theta 1$ and $\theta 2$. As illustrated, these angles are measured in mutually perpendicular planes, and one angle, in this case angle $\theta 1$, is usually substantially larger than the other. As is characteristic of laser diodes, the emitted laser beam LB will be plane-polarized in a plane P that is parallel to the major axis A' of the expanding elliptical cross-section of the beam. The minor axis A" of the elliptical cross-section is, of course, perpendicular to the major axis A'.

Figure 2:
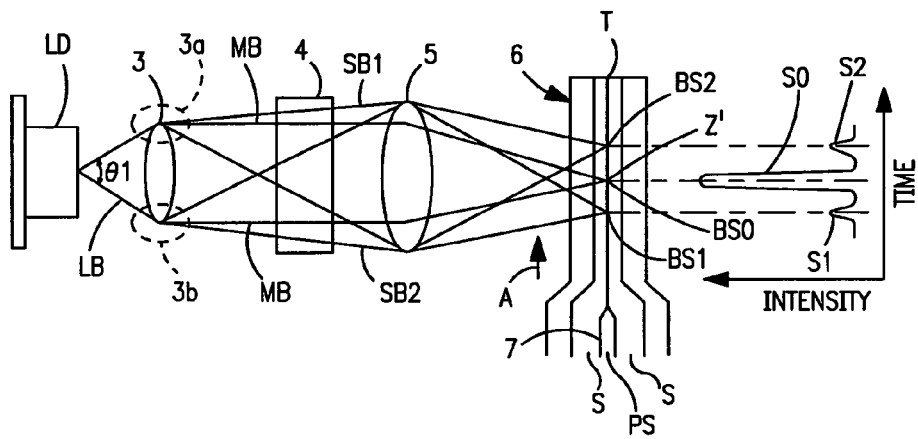
FIGS. 2 and 3 are schematic illustrations of prior art optical systems for focusing a diverging laser beam at a desired location within an optical flow cell of a flow cytometer.

In FIG. 2, the laser diode LD of FIG. 1 is shown as being embodied in a flow cytometer of the earlier type described above. A particle sample PS containing particles to be analyzed, e.g., blood cells, is introduced by a nozzle 7 into an optically-transparent flow cell 6 in the direction of arrow A. A sheath liquid S is supplied to the flow cell in such a manner as to surround the particle stream provided by nozzle 7, and thereby serves to hydrodynamically constrain the flow of the particle stream to the central axis of the flow cell, which is commonly vertically disposed. The rate of flow of the sheath fluid, in combination with the rate at which the particle sample is introduced by the nozzle 7, causes the particles to pass, one-at-a-time, through a particle interrogation zone Z' located at the center of the flow cell. The diverging laser beam LB emitted by the laser diode is collimated by a collimating lens, 3 and the resulting collimated main beam MB is passed through the combination of a cylindrical lens 4 and a condensing lens 5 to bring the main beam to an elliptical spot focus at the particle-interrogation zone. For the reasons noted above, it was conventional in the art to orient the laser diode so that major axis A' of its elliptical output beam extended parallel to the (normally vertical) particle path through the flow cell. (Note, in this orientation, the plane of polarization P of the laser beam also extends parallel to the particle path.) Notwithstanding this vertical orientation of the elliptical beam, the beam is brought to an elliptical spot focus in which the minor axis of the focused spot extends parallel to the particle path. This provides the technical advantages noted above.

With the laser diode orientation shown in FIG. 2, the collimating lens 3 will usually truncate a portion of the diverging laser beam in the plane in which the beam is expanding the faster, i.e., in the vertical plane in which angle θ1 is measured. Assuming the collimating lens is centered with respect to the diverging laser beam, this truncation gives rise to a pair of spurious beams SB1 and SB2 of relatively low intensity which appear to emanate from opposite sides 3a and 3b of the collimating lens 3 where the truncation takes place. In addition to focusing the main beam as an elliptical spot as described above, lenses 4 and 5 act to focus these spurious beams as beam spots (or light lobes) BS1 and BS2 on opposite sides of the focused beam spot BS of the main beam MB. As shown, the respective intensities S1 and S2 of these spurious beam spots are substantially lower than the intensity S0 of the main beam; nevertheless, these spurious beam spots are located directly on the particle path through the flow cell. Thus, each particle passing through the flow cell will be irradiated at three locations, only one of which (the middle location) is desirable. The light-scatter and fluorescence detectors, discussed below, will then receive signals from the spurious beams, thereby necessitating a scheme for ignoring these signals in the particle-differentiation process.

Figure 3:
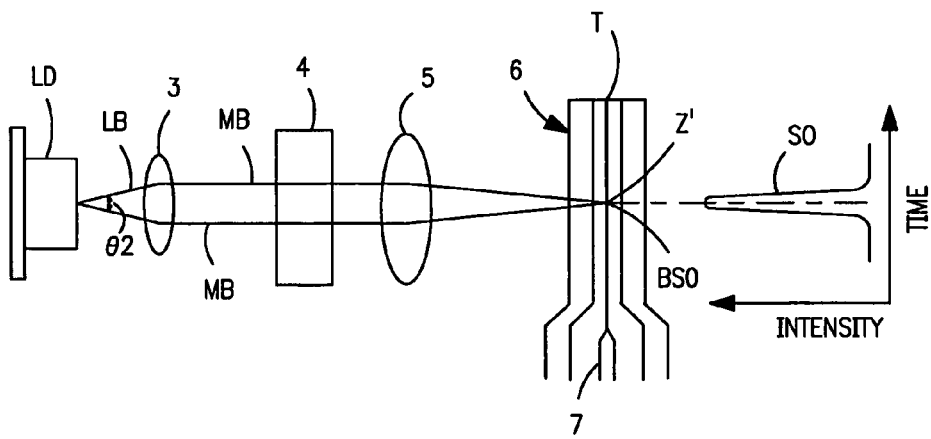

In the flow cytometer schematically illustrated in FIG. 3, it will be appreciated that the laser diode LD of FIGS. 1 and 2 has been rotated by 90 degrees so that the diverging laser beam LB now expands in the plane of the drawing and in the plane of the particle path at its smaller angle θ2. In this orientation of the laser diode, the major axis A' of its expanding elliptical output beam now extends in a horizontal plane, perpendicular to the particle path and to the plane of the drawing. Thus, while portions of the laser beam are still truncated by the collimating lens, the resulting spurious beam spots BS1 and BS2 (shown in FIG. 2) are now located on opposite sides of the particle path, rather than in alignment therewith. Note, this orientation of the laser diode also has the effect of orienting the plane of polarization P of the laser beam in a horizontal plane, perpendicular to the particle path. Thus, while the beam spots BS1 and BS2 are no longer located in a position to irradiate the particles passing through the flow cell, the plane of polarization of the beam is now problematic.

Figure 4A:
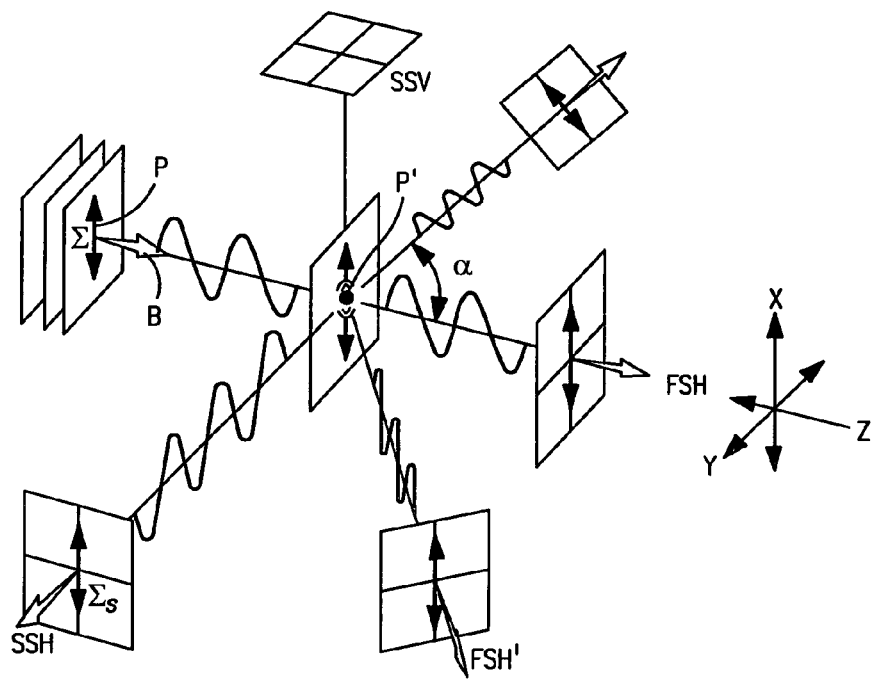
FIGS. 4A and 4B illustrate the effect on light scatter of a change in the plane of polarization of a plane-polarized light source.
Figure 4B:
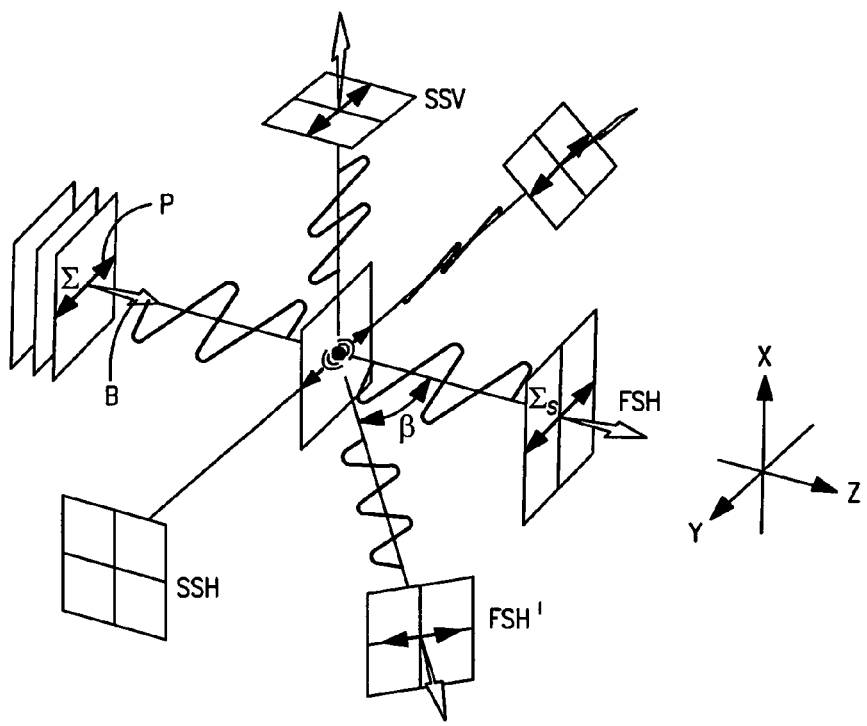

Referring to FIGS. 4A and 4B, it will be seen in FIG. 4A that a small particle P' irradiated by a plane-polarized light beam B that is polarized in the vertical X/Z plane, as indicated by the vector E, will act to scatter light in the horizontal Y/Z plane as shown. The scattered light in the horizontal plane, including the forward scatter FSH, side-scatter SSH, and the forward scatter FSH' at all intermediate angles, will retain its vertical polarization, and its intensity, measured at any angle in the horizontal plane, will be determined only by the physical and optical properties of the irradiated particle. Note, however, that the intensity of light scattered forwardly in the vertical X/Z plane will depend on the angle of measurement ∂ and, as angle ∂ approaches 90 degrees (measured with respect to the horizontal Y/Z plane) to a position in which the forwardly scattered light is directed vertically upwards (or downwards) and thereby becomes side-scattered light SSV in the vertical direction, the intensity of such scattered light will approach zero, as indicated. In effect, the wave oscillation in the vertical plane of polarization acts to cancel out the scattered beam intensity in the vertical direction. Similarly, as shown in FIG. 4B, if the beam source is rotated by 90 degrees so that its plane of polarization is now horizontal, i.e., in the Y/Z plane, the intensity of the light scattered in the vertical (X/Z) plane will be unaffected by this beam source orientation, but the light scattered in the horizontal (Y/Z) plane will depend on the angle β at which the measurement is made. Notice, the intensity of the side-scattered light SSH in the horizontal plane will become zero as the angle β approaches 90 degrees. Applying this information to the flow cytometer environment described above, it will be understood why the side-scatter signal is undetectable with the diode laser orientation shown in FIG. 3. As so oriented, the scattering conditions of FIG. 4B apply, and there is no side-scatter signal to detect.

Figure 5:
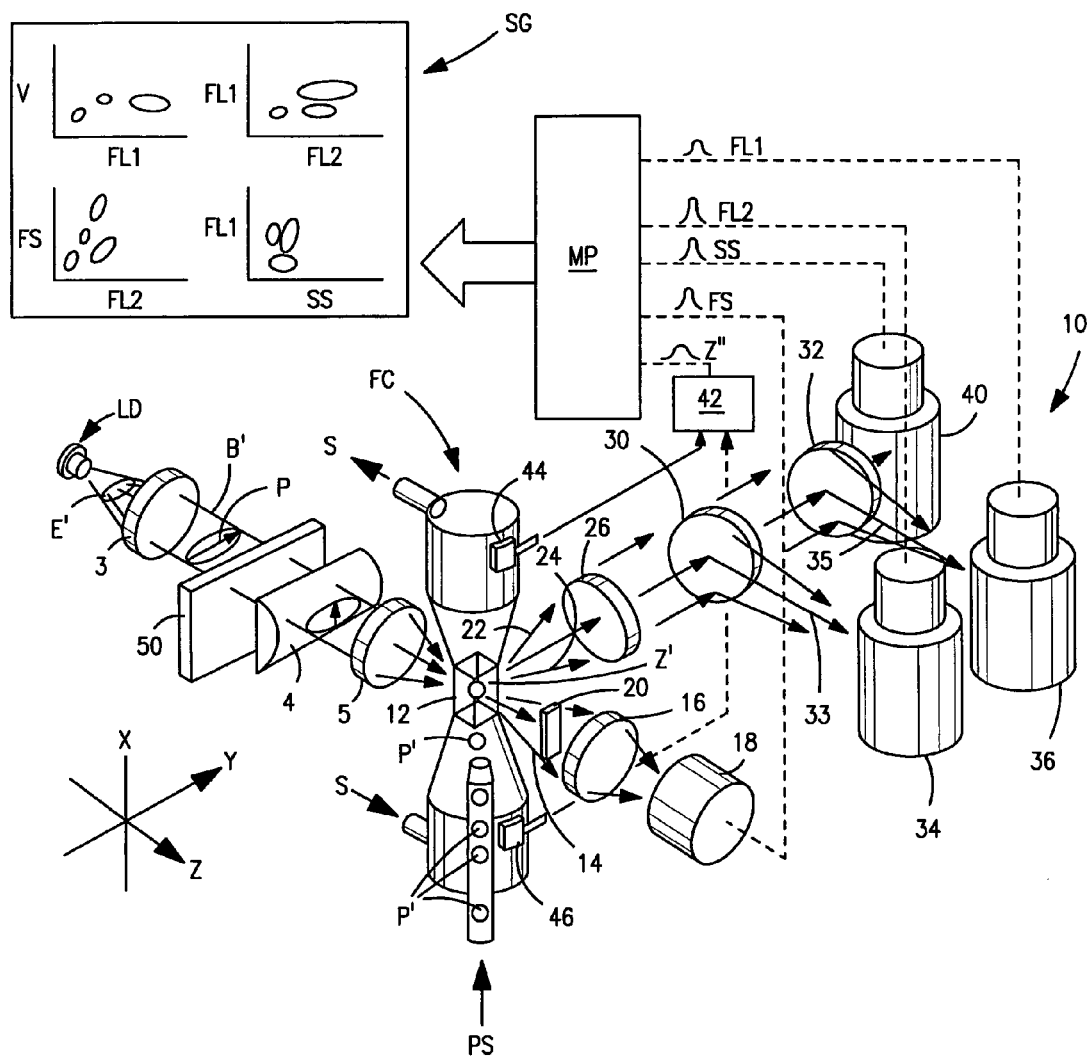
FIG. 5 is a perspective schematic illustration of a flow cytometer embodying the present invention

In view of the foregoing discussion, FIG. 5 schematically illustrates a flow cytometer 10 of the type in which the invention has utility and in which the present invention is embodied. As shown, the flow cytometer of the invention includes an optical flow cell FC through which a particle sample PS containing different particles P' to be characterized is caused to flow. The sample may comprise, for example, a whole blood sample in which the particles to be characterized are in the form of various types of blood cells (e.g., monocytes, lymphocytes, basophils, etc.). The flow cell comprises an optically transparent housing 12 that defines a narrow central channel through which the particles flow, one-at-a-time, while being irradiated by a focused laser beam B' provided by a laser diode LD. As shown, the laser diode is oriented so that its diverging elliptical output beam expands in a horizontal plane faster than in the vertical plane, whereby the aforementioned spurious beam spots are located on opposite sides of and outside the vertical particle through the flow cell, as discussed above with reference to FIG. 3. Upon passing through the particle-interrogation zone Z and being irradiated by the focused laser beam, each individual particle will scatter beam light and emit fluorescent radiation according to the type of particle irradiated. Forwardly scattered light 14 will be collected by a lens 16 and focused onto a suitable photodetector 18, and the output FS of the latter is applied to a microprocessor MP. Axial beam light is absorbed by a suitable light stop 20. Side-scattered light 22, i.e., beam light scattered at 90 degrees in the horizontal (Y/Z) plane, together with multicolor fluorescent light 24 emitted by fluorochromes carried by the selected particles, is collected and collimated by a lens 26, and the resulting collimated beam 28 is passed or reflected by a pair of dichroic mirrors 30, 32 arranged at 45 degrees to the collimated beam path. Side-scattered light 33 is reflected by mirror 30 to a suitable photodetector 34, typically a photomultiplier tube. Fluorescent light 35 of a first wavelength transmitted by mirror 30 and reflected by mirror 32 is directed to a second photodetector 36 that, again, is preferably a photomultiplier tube. Fluorescent light of a second wavelength that passes through both mirrors 30 and 32 is detected by a third photodetector 40, also preferably of the photomultiplier tube type. The respective outputs SS, FL1 and FL2 of photodetectors 34, 36 and 40 are fed to the microprocessor for processing. In addition to the light-scatter and fluorescence signals obtained from each particle passing through the flow cell, it is common to detect an impedance signal Z representing the Coulter volume of each particle interrogated. Such signal is derived by passing a constant-current through the interrogation zone of the flow cell and monitoring changes in current as occasioned by the electrical impedance of a particle in the zone; the larger the particle, the larger the change in current. A constant-current circuit 42, connected between a pair of electrodes 44,46 arranged on opposite sides of the particle-interrogation, provides the requisite current through the zone and operates to detect particle-induced changes in such current. The output Z" of circuit 42 is also fed to the microprocessor. Upon simultaneously processing the FL1, FL2, SS, FS and Z" input signals in accordance with one or more known algorithms, the microprocessor provides an output, typically in the form of a plurality of scattergrams SG, indicating the relative numbers and different types of particles in the particle sample PS.

As indicated above, a laser diode oriented as discussed with reference to FIG. 3 is problematic in that the plane of polarization P of the laser beam is perpendicular to the direction of particle flow. As shown in the flow cytometer of FIG. 5, the major axis of the expanding ellipse E' is in the horizontal plane, as is the major axis of the collimated beam that has passed through the collimating lens 3. Since the plane of polarization P of the beam will be parallel to the major axis, FIG. 4A shows that side-scattered radiation in the horizontal plane will be canceled out by wave vibrations in the horizontal plane. Thus, in accordance with the invention, an optical element 50 is positioned in the laser beam B', preferably in the collimated portion of the beam between the collimating lens 3 and the cylindrical lens 4. Element 50 has the effect of rotating the plane of polarization of the beam by an amount sufficient to orient the plane of polarization of the laser beam so that it is now substantially parallel to the (vertical) particle path through the flow cell. Accordingly, the benefit of rotating the laser diode to eliminate the undesirable spurious beam spots is combined with the benefit of being able to detect side-scattered light since the plane of polarization is as required to detect such side scattered light. Preferably, element 50 operates to rotate the plane of polarization of the laser beam by 90 degrees, and it takes the form of a conventional half-wave plate. Alternatively, element 50 may be in the form of two quarter-wave plates arranged in tandem.

While the invention has been described with reference to a preferred embodiment, it will be appreciated that various changes can be made without departing from the spirit of the invention. Such changes are intended to fall within the scope of the appended claims.

What is claimed is:

1. A flow cytometer comprising:
   (a) an optical flow cell having a particle-interrogation zone through which particles to be characterized can be made to pass, one-at-a-time, along a substantially linear particle path;
   (b) a laser for producing a plane-polarized laser beam, said laser being oriented so that the plane of polarization of said laser beam is perpendicular to the particle path;
   (c) a beam-shaping lens system for focusing said laser beam as an elliptical spot centered on said particle path within said particle-interrogation zone, the minor axis of said elliptical spot being arranged parallel to said particle path;
   (d) a side-scatter photodetector positioned to detect a portion of said laser beam upon being scattered by particles irradiated by said focused elliptical spot in a direction substantially perpendicular to said particle path and to the direction from which said laser beam irradiates a particle at said particle-interrogation zone; and
   (e) a polarization-rotating optical element positioned in said laser beam between said laser and said optical flow cell, said optical element serving to rotate the plane of polarization of said laser beam before said laser beam irradiates particles at said particle-interrogation zone.

2. The apparatus as defined by claim 1 wherein said polarization-rotating optical element serves to rotate the plane of polarization of said laser beam by an amount sufficient to render the plane of polarization of the particle-irradiating laser beam substantially parallel to said particle path.

3. The apparatus as defined by claim 2 wherein said polarization-rotating optical element operates to rotate the plane of polarization of said laser beam by 90 degrees.

4. The apparatus as defined by claim 3 wherein said polarization-rotating optical element comprises a half-wave plate.

5. The apparatus as defined by claim 3 wherein said polarization-rotating optical element comprises a pair of quarter-wave plates.

6. A flow cytometer comprising:
   (a) an optical flow cell having a linear particle path along which particles to be characterized can be made to pass seriatim;
   (b) a laser diode for producing a plane-polarized laser beam of elliptical cross-section having mutually perpendicular major and minor axes, said laser diode being arranged so that the major axis of said elliptical cross-section extends perpendicular to said particle path;
   (c) a lens system for focusing said laser beam to an elliptical spot having mutually perpendicular major and minor axes on said particle path, said spot being oriented so that said minor axis of the focused spot is parallel to said particle path;
   (d) a side-scatter photodetector positioned to detect laser radiation scattered in a direction substantially perpendicular to the direction of particle flow and to the direction at which said laser beam irradiates a particle moving along said particle path; and
   (e) an optical element positioned in said laser beam and functioning to rotate the plane of polarization of said laser beam by 90 degrees before said laser beam irradiates particles on said particle path.

7. The apparatus as defined by claim 6 wherein said optical element comprises a half-wave plate.

8. The apparatus as defined by claim 6 wherein said optical element comprises a pair of quarter-wave plates arranged in tandem.

9. A flow cytometer comprising:
   (a) an optical flow cell having a particle-interrogation zone through which particles to be characterized can be made to pass, one-at-a-time, along a substantially linear particle path;
   (b) a laser that produces a plane-polarized laser beam of expanding elliptical cross-section having mutually perpendicular major and minor axes, said laser beam being plane-polarized in a plane parallel to the major axis of the expanding elliptical cross-section, said being oriented with respect to said optical flow cell so that said plane of polarization is substantially perpendicular to said linear particle path;
   (c) a collimating lens for collecting and collimating a major portion of said laser beam to provide a collimated laser beam, said collimating lens further operating to truncate a portion of said expanding elliptical cross-section and thereby give rise to spurious light sources appearing at opposite sides of said collimating lens;

(d) a beam-shaping lens system for (i) focusing the collimated laser beam as an elliptical spot centered on the linear particle path within the particle-interrogation zone, and (ii) condensing light from said spurious light sources as spurious light spots on opposite sides of, and along the major axis of, the focused elliptical spot, said beam-shaping lens system being effective to orient said focused elliptical spot so that its minor axis extends parallel to said particle path, thereby positioning the spurious light spots on opposite sides of and spaced from said particle path;

(e) a side-scatter photodetector positioned to detect laser radiation scattered from a particle irradiated by said focused elliptical spot in a direction substantially perpendicular to the particle path and to the direction at which said laser beam irradiates a particle at said particle-interrogation zone; and (f) a polarization-rotating optical element, positioned in said laser beam and adapted to rotate the plane of polarization of said laser beam by 90 degrees before said laser beam irradiates particles at said particle-interrogation zone.

10. The apparatus as defined by claim 9 wherein said polarization-rotating optical element is positioned in the collimated portion of said laser beam.

11. The apparatus as defined by claim 9 wherein said polarization-rotating optical element comprises a half-wave plate.

12. The apparatus as defined by claim 9 wherein said polarization-rotating optical element comprises a pair of quarter-wave plates arranged in tandem.

* * * * *